(12) United States Patent
Rheinberger et al.

(10) Patent No.: US 10,376,343 B2
(45) Date of Patent: Aug. 13, 2019

(54) LITHIUM SILICATE GLASS CERAMIC AND GLASS WITH RUBIDIUM OXIDE CONTENT

(71) Applicant: Ivoclar Vivadent AG, Schaan (LI)

(72) Inventors: Volker Rheinberger, Vaduz (LI); Markus Rampf, Lachen (CH); Marc Dittmer, Feldkirch (AT); Christian Ritzberger, Grabs (CH); Wolfram Höland, Schaan (LI); Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 847 days.

(21) Appl. No.: 14/784,149

(22) PCT Filed: Apr. 8, 2014

(86) PCT No.: PCT/EP2014/057040
§ 371 (c)(1),
(2) Date: Oct. 13, 2015

(87) PCT Pub. No.: WO2014/170168
PCT Pub. Date: Oct. 23, 2014

(65) Prior Publication Data
US 2016/0051349 A1    Feb. 25, 2016

(30) Foreign Application Priority Data
Apr. 15, 2013 (EP) ..................... 13163828

(51) Int. Cl.
| | | |
|---|---|---|
| *A61L 27/10* | (2006.01) | |
| *C03C 10/00* | (2006.01) | |
| *A61K 6/00* | (2006.01) | |
| *A61K 6/02* | (2006.01) | |
| *A61K 6/027* | (2006.01) | |
| *A61L 27/30* | (2006.01) | |
| *C03C 8/08* | (2006.01) | |
| *C03C 4/00* | (2006.01) | |
| *A61C 13/083* | (2006.01) | |
| *C03C 3/097* | (2006.01) | |
| *C03C 3/112* | (2006.01) | |

(52) U.S. Cl.
CPC ........ *A61C 13/0835* (2013.01); *A61K 6/0094* (2013.01); *A61K 6/024* (2013.01); *A61K 6/025* (2013.01); *A61K 6/0205* (2013.01); *A61K 6/026* (2013.01); *A61K 6/0235* (2013.01); *A61K 6/0273* (2013.01); *A61L 27/10* (2013.01); *A61L 27/306* (2013.01); *C03C 3/097* (2013.01); *C03C 3/112* (2013.01); *C03C 4/0021* (2013.01); *C03C 8/08* (2013.01); *C03C 10/00* (2013.01); *C03C 10/0009* (2013.01); *A61L 2430/12* (2013.01); *C03C 2205/06* (2013.01)

(58) Field of Classification Search
None
See application file for complete search history.

(56) References Cited

U.S. PATENT DOCUMENTS

| | | |
|---|---|---|
| 2,684,911 A | 7/1954 | Stookey |
| 3,006,775 A | 10/1961 | Chen |
| 3,022,180 A | 2/1962 | Morrissey et al. |
| 3,161,528 A | 12/1964 | Eppler |
| 3,252,778 A | 5/1966 | Goodman et al. |
| 3,732,087 A | 5/1973 | Grossman |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A | 6/1993 | Beall et al. |
| 5,507,981 A | 4/1996 | Petticrew |
| 5,628,564 A | 5/1997 | Nenyei et al. |
| 5,691,256 A | 11/1997 | Taguchi et al. |
| 5,698,482 A | 12/1997 | Frank et al. |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,938,959 A | 8/1999 | Wang |
| 5,968,856 A | 10/1999 | Schweiger et al. |

(Continued)

FOREIGN PATENT DOCUMENTS

| | | |
|---|---|---|
| CA | 2163792 A1 | 12/1994 |
| CA | 2213390 A1 | 3/1998 |

(Continued)

OTHER PUBLICATIONS

International Preliminary Report on Patentability of PCT/EP2014/057040, dated Oct. 20, 2015, 7 pages.

E. Apel et al., "Influence of Zr02 on the crystallization and properties of lithium disilicate glass-ceramics derived from multi-component system", Journal of European Ceramic Society, 2007, 27, 1571-1577.

Dr. Bernhard Durschang, "Report of Results", Fraunhofer Institute for Silicate Research ISC Glass and Mineral Materials, 2015.

P.W. McMillan et al., "The Structure and Properties of a Lithium Zinc Silicate Glass-Ceramic", Journal of Material Science 1966, I. 269-279.

J. Deubener et al., "Induction time analysis of nucleation and crystal grown in di- and metasilicate glasses", Journal of Non-Crystalline Solids 1993, 163, 1-12.

(Continued)

*Primary Examiner* — Barbara J Musser

(74) *Attorney, Agent, or Firm* — Ann M. Knab; Thad McMurray

(57) ABSTRACT

The invention relates to the use of lithium silicate glass ceramics and glasses with rubidium oxide content for coating an oxide ceramic, a metal or an alloy.

46 Claims, No Drawings

(56) References Cited

U.S. PATENT DOCUMENTS

| | | | |
|---|---|---|---|
| 6,066,584 A | 5/2000 | Krell et al. |
| 6,095,682 A | 8/2000 | Hollander et al. |
| 6,106,747 A | 8/2000 | Wohlwend |
| 6,121,175 A | 9/2000 | Drescher et al. |
| 6,048,589 A | 11/2000 | Suzuki |
| 6,157,004 A | 12/2000 | Bizzio |
| 6,163,020 A | 12/2000 | Bartusch et al. |
| 6,174,827 B1 | 1/2001 | Goto et al. |
| 6,252,202 B1 | 6/2001 | Zychek |
| 6,267,595 B1 | 7/2001 | Gratz |
| 6,270,876 B1 | 8/2001 | Abe et al. |
| 6,287,121 B1 | 9/2001 | Guiot et al. |
| 6,342,458 B1 | 1/2002 | Schweiger et al. |
| 6,376,397 B1 | 4/2002 | Petticrew |
| 6,420,288 B2 | 7/2002 | Schweiger et al. |
| 6,441,346 B1 | 8/2002 | Zychek |
| 6,455,451 B1 | 9/2002 | Brodkin et al. |
| 6,485,849 B2 | 11/2002 | Petticrew |
| 6,514,893 B1 | 2/2003 | Schweiger et al. |
| 6,517,623 B1 | 2/2003 | Brodkin et al. |
| 6,593,257 B1 | 7/2003 | Nagata et al. |
| 6,706,654 B2 | 3/2004 | Van Der Zel |
| 6,802,894 B2 | 10/2004 | Brodkin et al. |
| 6,818,573 B2 | 11/2004 | Petticrew |
| 7,162,321 B2 | 1/2007 | Luthardt et al. |
| 7,183,232 B2 | 2/2007 | Apel |
| 7,316,740 B2 | 1/2008 | Rheinberger et al. |
| 7,452,836 B2 | 11/2008 | Apel et al. |
| 7,655,586 B1 | 2/2010 | Brodkin et al. |
| 7,806,694 B2 | 10/2010 | Brodkin et al. |
| 7,816,291 B2 | 10/2010 | Schweiger et al. |
| 7,867,930 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,042,358 B2 | 10/2011 | Schweiger et al. |
| 8,047,021 B2 | 11/2011 | Schweiger et al. |
| 8,444,756 B2 | 5/2013 | Schweiger et al. |
| 8,778,075 B2 | 7/2014 | Ritzberger et al. |
| 9,101,439 B2 | 8/2015 | Ritzberger et al. |
| 9,757,217 B2* | 9/2017 | Burke .................... C03C 3/083 |
| 2001/0006174 A1 | 7/2001 | Brennan |
| 2001/0031446 A1 | 10/2001 | Petticrew |
| 2002/0010063 A1 | 1/2002 | Schweiger et al. |
| 2002/0022563 A1 | 2/2002 | Schweiger et al. |
| 2002/0031670 A1 | 3/2002 | Goto et al. |
| 2002/0035025 A1 | 3/2002 | Schweiger et al. |
| 2002/0160694 A1 | 10/2002 | Wood et al. |
| 2003/0073563 A1 | 4/2003 | Brodkin et al. |
| 2004/0182538 A1 | 9/2004 | Lambrecht |
| 2004/0232576 A1* | 11/2004 | Brodkin ................. C03C 3/091 264/16 |
| 2005/0098064 A1 | 5/2005 | Schweiger et al. |
| 2005/0127544 A1 | 6/2005 | Brodkin et al. |
| 2006/0082033 A1 | 4/2006 | Hauptmann et al. |
| 2006/0139091 A1 | 6/2006 | Fratti |
| 2006/0257823 A1 | 11/2006 | Pfeiffer et al. |
| 2006/0257824 A1 | 11/2006 | Pfeiffer et al. |
| 2007/0023971 A1 | 2/2007 | Saha et al. |
| 2008/0120994 A1 | 5/2008 | Schweiger et al. |
| 2008/0199823 A1 | 8/2008 | Miller |
| 2009/0023574 A1 | 1/2009 | Holand et al. |
| 2009/0038344 A1 | 2/2009 | Apel et al. |
| 2009/0038508 A1 | 2/2009 | Apel et al. |
| 2009/0042166 A1 | 2/2009 | Craig et al. |
| 2009/0256274 A1 | 10/2009 | Castillo |
| 2009/0258778 A1 | 10/2009 | Castillo |
| 2010/0083706 A1 | 4/2010 | Castillo |
| 2011/0256409 A1 | 10/2011 | Ritzberger et al. |
| 2012/0094822 A1 | 4/2012 | Castillo et al. |
| 2012/0148988 A1 | 6/2012 | Castillo et al. |
| 2012/0248642 A1 | 10/2012 | Ritzberger et al. |
| 2012/0309607 A1 | 12/2012 | Durschang et al. |
| 2014/0135202 A1* | 5/2014 | Ritzberger .............. C03C 3/083 501/32 |
| 2014/0141960 A1 | 5/2014 | Borczuch-Laczka et al. |
| 2014/0200129 A1 | 7/2014 | Durschang |
| 2014/0225290 A1* | 8/2014 | Ritzberger .............. C03C 3/095 264/17 |
| 2015/0140274 A1* | 5/2015 | Burke .................... A61K 6/026 428/156 |
| 2015/0374465 A1* | 12/2015 | Burke ................ A61C 13/0022 433/201.1 |

FOREIGN PATENT DOCUMENTS

| | | |
|---|---|---|
| CA | 2239865 A1 | 12/1998 |
| CA | 2239869 A1 | 12/1998 |
| CA | 2252660 A1 | 5/1999 |
| DE | 2451121 A1 | 5/1975 |
| DE | 4303458 C1 | 1/1994 |
| EP | 1152641 A2 | 11/2001 |
| EP | 1688397 A1 | 8/2006 |
| GB | 752243 A | 7/1956 |
| GB | 2284655 A | 6/1995 |
| JP | H10323354 A | 12/1998 |
| JP | 11-74418 A | 3/1999 |
| JP | 2005-062832 A | 3/2005 |
| WO | 2004021921 A1 | 3/2004 |
| WO | 2007028787 A1 | 3/2007 |
| WO | 2012082156 A1 | 6/2012 |
| WO | WO-2013167723 A1 * | 11/2013 ............. A61K 6/026 |

OTHER PUBLICATIONS

W. Holand et al., "Glass-ceramic technology", American Chemical Society 2002, Westerville OH, USA.

W. Holand et al., "Control of nucleation in glass ceramics", Phil. Trans. Soc. Lond. A 2003, 361, 575-589.

W. Holand et al., "Principles and phenomena of bioengineering with glass-ceramics of dental restoration", Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58,385-391.

Von Clausbruch, et al., "Effect of ZnO on the Crystallization, Microstructure, and Properties of Glass-Ceramics in the $SiO_2$—$Li_2O$—$K_2O$—$P_2O_5$ System," Glastech. Ber. Glass Sci. Technol. 74(8):223-229(2001).

Von Clausbruch, et al., "Effect of $P_2O_5$ on the Crystallization and Microstructure of Glass-Ceramics in the $SiO_2$—$Li_2O$—Zn)—$P_2O_5$ System," Glastech. Ber. Glass Sci. Technol. 74(8):223-229(2001).

Stookey, S.D., "Chemical Machining of Photosensitive Glass," Ind. Eng. Chem. 45:115-118 (1993).

Oliveria et al., "Sintering and Crystallization of a GlassPowder in the $Li_2O$—$ZrO_2$—$SiO_2$ System," J. Amer. Ceramic Soc. 81(3):777-780 (1998).

Montedo, et al., "Low Thermal Expansion Sintered LZSA Glass-Ceramics," American Ceramic Society Bulletin, vol. 87, No. 7, pp. 34-40.

Giassi, et al., "Injection Moulding of $LiO_2$—$ZrO_2$—$SiO_2$—$Al_2O_3$ (LZSA) Glass Ceramics," Glass Technol., 46(3), (2005). 277-280 (2005).

http://en.wikipedia.org/wiki/Nucleation ; Sep. 20, 2012.

* cited by examiner

LITHIUM SILICATE GLASS CERAMIC AND GLASS WITH RUBIDIUM OXIDE CONTENT

CROSS-REFERENCE TO RELATED APPLICATIONS

This application is a National Stage application of International Patent Application No. PCT/EP2014/057040 filed on Apr. 8, 2014, which claims priority to European Patent Application No. 13163828.0 filed on Apr. 15, 2013, the disclosures of which are incorporated herein by reference in their entirety.

The invention relates to lithium silicate glass ceramic and lithium silicate glass which comprise rubidium oxide and are characterized by a linear coefficient of thermal expansion that is adjustable in a broad range of in particular 9.0 to 14.0·$10^{-6}$ $K^{-1}$ and are therefore suitable primarily in the dental field for veneering oxide ceramic restorations and metal restorations.

In dentistry, dental restorations are usually veneered with ceramic layers in order to match the appearance of the restoration to that of the natural teeth. Such veneered restorations are also called veneer ceramics. In order to avoid stresses between the restoration material to be veneered and the ceramic layer, it is necessary for the coefficients of thermal expansion of the ceramic materials to be adapted to that of the restoration material.

Glass ceramics have already been used in the past to coat or veneer oxide ceramics, such as zirconium oxide ceramics. These include feldspar-based ceramics or fluoroapatite glass ceramics.

Lithium disilicate glass ceramics are also known which, because of their high translucence and very good mechanical properties, are used in particular in the dental field and primarily for producing dental crowns and small bridges. The known lithium silicate glass ceramics usually contain as main components $SiO_2$, $Li_2O$, $Al_2O_3$, $Na_2O$ or $K_2O$, and nucleating agents such as $P_2O_5$.

EP 0 885 855 A2 and EP 0 885 856 A2 describe apatite-containing glass ceramics with excellent optical and chemical properties and a strength in the region of 110 MPa, which are suitable for veneering $ZrO_2$ frameworks.

WO 2004/021921 A1 describes a glass for veneering $ZrO_2$, but which only has a low strength.

EP 1 253 116 A1 describes a mixture of a lithium silicate glass with leucite crystals for veneering metal frameworks. This glass also has only an inadequate strength.

WO 2012/082156 A1 describes a lithium silicate product for veneering metal frameworks with a coefficient of expansion $CTE_{100-400° C.}$ of from 12 to 13.5·$10^{-6}$ $K^{-1}$ and strengths of up to 300 MPa.

EP 2 377 831 A1 describes a lithium silicate glass ceramic with $ZrO_2$ content. The coefficient of expansion of the glass ceramic is not suitable for veneering metal frameworks.

In order for a dental glass ceramic to be able to be used for veneering the whole spectrum of the customarily used restoration materials, such as from dental metals and alloys to oxide ceramics, it is necessary for its coefficient of expansion to be adjustable in a broad range. Moreover, the glass ceramics must satisfy high requirements with regard to their optical and mechanical properties and in particular must have a very high strength.

Known glass ceramics and glasses often do not satisfy the requirement for coefficients of thermal expansion that are adjustable in a broad range and for adequate strength. Further, with the known glass ceramics the alkaline earth metal oxide BaO as well as the alkali metal oxides $K_2O$ and/or $Na_2O$ are as a rule present as essential components which are clearly required there for the production of the glass ceramics and in particular the formation of the usually sought lithium disilicate main crystal phase.

There is therefore a need for lithium silicate glass ceramics in which the linear coefficient of thermal expansion $CTE_{100-400° C.}$ is adjustable over a broad range and in particular in the range of from 9.0 to 14.0·$10^{-6}$ $K^{-1}$ and preferably in the range of from 9.6 to 12.8·$10^{-6}$ $K^{-1}$. Further, they should also be able to be produced without the alkali metal oxides $K_2O$ or $Na_2O$, previously regarded as necessary, as well as in particular without the alkaline earth metal oxide BaO, and be suitable in particular for veneering dental restorations, including oxide ceramic restorations and metal restorations, primarily on the basis of their optical and mechanical properties.

This object is achieved by the use of a lithium silicate glass ceramic or a lithium silicate glass according to any one of claims 1 to 14. A subject of the invention is likewise the method according to claims 15 to 20, the composite material according to claim 21, the lithium silicate glass ceramic according to claim 22 and the lithium silicate glass according to claim 23.

The use according to the invention is characterized in that a lithium silicate glass ceramic or a lithium silicate glass which comprises the following components

| Component | wt.-% |
|---|---|
| $SiO_2$ | 56.0 to 73.0 |
| $Li_2O$ | 13.0 to 19.0 |
| $Rb_2O$ | 3.0 to 9.0 |
| $Al_2O_3$ | 2.0 to 5.0 |
| $P_2O_5$ | 2.0 to 6.0 | is used for coating a substrate selected from oxide ceramics, metals and alloys.

It has surprisingly been shown that the lithium silicate glass ceramic according to the invention has a linear coefficient of thermal expansion $CTE_{100-400° C.}$ which is easily adjustable in a broad range of in particular 9.0 to 14.0·$10^{-6}$ $K^{-1}$ and preferably 9.6 to 12.8·$10^{-6}$ $K^{-1}$, and moreover has excellent optical and mechanical properties such as high strength and fracture toughness. This glass ceramic is therefore suitable for coating both oxide ceramics as well as metals and alloys. It is particularly surprising that the formation of a glass ceramic with lithium meta- and/or disilicate as main crystal phase is successful even in the absence of various components regarded as necessary for conventional glass ceramics, such as in particular $K_2O$, $Na_2O$ and BaO. The formation of the glass ceramic according to the invention can also be achieved by the use of the lithium silicate glass according to the invention, which represents a precursor for the lithium silicate glass ceramic and can be converted to same before, during or after the application to the substrate.

It is preferred that the lithium silicate glass ceramic used according to the invention and the lithium silicate glass used according to the invention comprise at least one and preferably all of the following components in the given amounts

| Component | wt.-% |
|---|---|
| $SiO_2$ | 56.9 to 72.0 |
| $Li_2O$ | 14.2 to 18.0 |
| $Rb_2O$ | 3.7 to 7.7 |

-continued

| Component | wt.-% |
| --- | --- |
| $Al_2O_3$ | 2.5 to 4.5 |
| $P_2O_5$ | 3.1 to 5.0 |
| $ZrO_2$ | 0 to 4.5, in particular 0 to 4.0 |
| Transition metal oxide | 0 to 7.5, in particular 0 to 7.0, | wherein the transition metal oxide is selected from the group consisting of oxides of yttrium, oxides of transition metals with an atomic number from 41 to 79 and mixtures of these oxides.

The lithium silicate glass ceramic and the lithium silicate glass preferably comprise 58.0 to 72.0, in particular 60.0 to 71.0 and preferably 63.0 to 70.0 wt.-% $SiO_2$.

It is also preferred that the lithium silicate glass ceramic and the lithium silicate glass comprise 14.4 to 17.5, in particular 14.5 to 17.0 and particularly preferably 14.8 to 16.0 wt.-% $Li_2O$.

In a preferred embodiment, the molar ratio of $SiO_2$ to $Li_2O$ is from 2.0 to 3.0, in particular from 2.2 to 2.6, preferably from 2.3 to 2.5 and particularly preferably about 2.4. In another preferred embodiment, the molar ratio of $SiO_2$ to $Li_2O$ is less than 2.0, in particular from 1.5 to 1.9, preferably from 1.6 to 1.8 and particularly preferably about 1.7.

It is preferred that the lithium silicate glass ceramic and the lithium silicate glass comprise 3.7 to 7.7 wt.-%, in particular 5.1 to 7.7 wt.-% and preferably 6.1 to 7.4 wt.-% $Rb_2O$.

It is also preferred that the lithium silicate glass ceramic and the lithium silicate glass comprise 2.5 to 4.0 wt.-%, in particular 3.0 to 3.5 wt.-% and preferably 3.2 to 3.4 wt.-% $Al_2O_3$.

The molar ratio of $Rb_2O$ to $Al_2O_3$ is preferably at least 0.1, in particular from 0.2 to 2.0, preferably from 0.25 to 1.25 and particularly preferably from 0.5 to 1.0.

The glass and the glass ceramic preferably comprise 3.2 to 4.5 wt.-% and in particular 3.4 to 4.0 wt.-% $P_2O_5$ as nucleating agent.

The lithium silicate glass ceramic used according to the invention and the lithium silicate glass used according to the invention can moreover also comprise additional components which are selected in particular from further oxides of monovalent elements, oxides of divalent elements, further oxides of trivalent elements, further oxides of tetravalent elements, further oxides of pentavalent elements, oxides of hexavalent elements, melt accelerators, colorants and fluorescent agents. In a preferred embodiment, the lithium silicate glass ceramic and the lithium silicate glass comprise additional components in an amount of from 0 to 20.0 wt.-%, in particular 0.1 to 10.0 wt.-%, preferably 0.5 to 7.5 wt.-% and most preferably 1.0 to 5.0 wt.-%.

The term "further oxides of monovalent elements" refers to oxides of monovalent elements and in particular alkali metal oxides with the exception of $Li_2O$ and $Rb_2O$. Examples of suitable further oxides of monovalent elements are $Na_2O$, $K_2O$, $Cs_2O$ and mixtures thereof and in particular $Na_2O$, $K_2O$ and mixtures thereof.

In an embodiment, the lithium silicate glass ceramic and the lithium silicate glass comprise 0.1 to 2.0 wt.-%, in particular 0.2 to 1.5 wt.-%, preferably 0.3 to 1.4 wt.-% and particularly preferably 0.5 to 1.0 wt.-% $Na_2O$. In a further embodiment, the lithium silicate glass ceramic and the lithium silicate glass comprise 0.1 to 2.0 wt.-%, in particular 0.2 to 1.6 wt.-%, preferably 0.4 to 1.5 wt.-% and particularly preferably 0.5 to 1.0 wt.-% $K_2O$. In a particularly preferred embodiment, the lithium silicate glass ceramic and the lithium silicate glass comprise less than 4.0 wt.-%, in particular less than 3.5 wt.-%, preferably less than 3.0 wt.-%, particularly preferably less than 2.5 wt.-% and most preferably less than 2.0 wt.-% $Na_2O$ and/or $K_2O$.

The lithium silicate glass ceramic and the lithium silicate glass preferably comprise less than 2.5 wt.-%, in particular less than 1.5 wt.-%, preferably less than 1.0 wt.-%, particularly preferably less than 0.5 wt.-% $Cs_2O$. They are most preferably substantially free of $Cs_2O$.

In particular the alkaline earth metal oxides, preferably MgO, CaO, SrO, BaO and mixtures thereof, and preferably CaO, SrO and mixtures thereof, come into consideration as oxides of divalent elements.

The lithium silicate glass ceramic and the lithium silicate glass preferably comprise less than 3.8 wt.-%, in particular less than 2.5 wt.-%, preferably less than 1.5 wt.-%, particularly preferably less than 0.5 wt.-% BaO. They are most preferably substantially free of BaO.

The term "further oxides of trivalent elements" refers to oxides of trivalent elements with the exception of $Al_2O_3$. Suitable oxides of trivalent elements are in particular $Y_2O_3$, $La_2O_3$, $Bi_2O_3$ and mixtures thereof, and preferably $Y_2O_3$ and $La_2O_3$.

The term "further oxides of tetravalent elements" refers to oxides of tetravalent elements with the exception of $SiO_2$. Examples of suitable further oxides of tetravalent elements are $TiO_2$, $GeO_2$ and $ZrO_2$.

The term "further oxides of pentavalent elements" refers to oxides of pentavalent elements with the exception of $P_2O_3$. Examples of suitable further oxides of pentavalent elements are $Ta_2O_5$ and $Nb_2O_5$.

Examples of suitable oxides of hexavalent elements are $WO3$ and $MoO_3$.

A glass and a glass ceramic which comprise at least one further oxide of monovalent elements, one oxide of divalent elements, at least one further oxide of trivalent elements, at least one further oxide of tetravalent elements, at least one further oxide of pentavalent elements and/or at least one oxide of hexavalent elements are preferred.

Examples of melt accelerators are fluorides.

Examples of colorants and fluorescent agents are oxides of d- and f-elements, such as the oxides of Ti, V, Sc, Mn, Fe, Co, Ta, W, Ce, Pr, Nd, Tb, Er, Dy, Gd, Eu and Yb. Metal colloids, e.g. of Ag, Au and Pd, can also be used as colorants and in addition can also act as nucleating agents. These metal colloids can be formed e.g. by reduction of corresponding oxides, chlorides or nitrates during the melting and crystallization processes. The metal colloids are preferably present in the glass ceramic in an amount of from 0.005 to 0.5 wt.-%.

The glass ceramic used according to the invention preferably has lithium metasilicate and/or lithium disilicate as main crystal phase. The term "main crystal phase" denotes the crystal phase which has the highest proportion by volume compared with the other crystal phases. If two crystal phases have approximately the same proportion by volume, these crystal phases can both be present as main crystal phases. In other embodiments, lithium metasilicate can be present as main crystal phase and lithium disilicate as secondary phase or lithium disilicate as main crystal phase and lithium metasilicate as secondary phase.

It has surprisingly been shown that the lithium silicate glass ceramic according to the invention has very good mechanical and optical properties even in the absence of components regarded as necessary for conventional glass ceramics. The combination of their properties even allows them to be used as dental material and in particular for coating dental restorations.

The lithium silicate glass ceramic according to the invention preferably has a fracture toughness, measured as $K_{IC}$ value, of at least about 2.0 MPa·m$^{0.5}$ and in particular at least about 2.3 MPa·m$^{0.5}$. This value was determined using the Vickers method and calculated using Niihara's equation. Further, it has a high biaxial breaking strength of preferably 180 to 700 MPa. Moreover, it displays a high chemical stability ascertained by mass loss after storage in acetic acid. The chemical stability is in particular less than 100 µg/cm$^2$. The biaxial breaking strength and the chemical stability were determined according to ISO 6872 (2008).

In a preferred embodiment, the glass ceramic comprises lithium metasilicate as main crystal phase. In particular the glass ceramic comprises more than 5 vol.-%, preferably more than 10 vol.-% and particularly preferably more than 15 vol.-% lithium metasilicate crystals, relative to the total glass ceramic. This lithium metasilicate glass ceramic is characterized by very good mechanical properties. It preferably has a bending strength in the range of about 180 to 300 MPa and/or a fracture toughness, measured as $K_{IC}$ value, of at least about 2.0 MPa·m$^{0.5}$ and in particular at least about 2.3 MPa·m$^{0.5}$. It can be formed e.g. by heat treatment of a corresponding lithium silicate glass and in particular of a corresponding lithium silicate glass with nuclei.

In a further particularly preferred embodiment, the glass ceramic comprises lithium disilicate as main crystal phase. In particular the glass ceramic comprises more than 10 vol.-%, preferably more than 20 vol.-% and particularly preferably more than 30 vol.-% lithium disilicate crystals, relative to the total glass ceramic. This lithium disilicate glass ceramic is characterized by particularly good mechanical properties. It preferably has a bending strength in the range of about 400 to 700 MPa and/or a fracture toughness, measured as $K_{IC}$ value, of at least about 2.0 MPa·m$^{0.5}$ and in particular at least about 2.3 MPa·m$^{0.5}$. It can be produced e.g. by heat treatment of the lithium metasilicate glass ceramic. However, it can also be formed by heat treatment of a corresponding lithium silicate glass or a corresponding lithium silicate glass with nuclei.

In particular $Li_3PO_4$, $SiO_2$ and $TiO_2$ come into question as further crystal phases of the lithium silicate glass ceramic.

In a further embodiment, a lithium silicate glass is used. This lithium silicate glass preferably comprises nuclei which are suitable for the formation of lithium metasilicate and/or lithium disilicate crystals. Such a lithium silicate glass with nuclei can be formed in particular by heat treatment of a corresponding lithium silicate glass. The lithium metasilicate glass ceramic according to the invention can then be formed by a further heat treatment, and in turn be converted to the lithium disilicate glass ceramic according to the invention by further heat treatment, or the lithium disilicate glass ceramic according to the invention can also preferably be formed directly from the glass with nuclei. Consequently, the lithium silicate glass, the lithium silicate glass with nuclei and the lithium metasilicate glass ceramic can be regarded as precursors for producing a high-strength lithium meta- or disilicate glass ceramic according to the invention. The lithium silicate glass is preferably converted to a glass ceramic as described above before, during or after application to the substrate.

To produce the lithium silicate glass, the procedure can be in particular that a mixture of suitable starting materials, such as carbonates, oxides, phosphates and fluorides, is melted at temperatures of in particular 1300 to 1600° C. for 2 to 10 h. To achieve a particularly high homogeneity, the obtained glass melt is poured into water in order to form a glass granulate, and the obtained granulate is then melted again. The melt can then be poured into moulds to produce blanks of the lithium silicate glass, so-called solid glass blanks or monolithic blanks. It is also possible to put the melt into water again in order to produce a granulate. This granulate can then be pressed, after grinding and optionally addition of further components, such as colorants and fluorescent agents, to form a blank, a so-called powder green compact. Finally, the lithium silicate glass can also be processed to form a powder after granulation.

The lithium silicate glass, e.g. in the form of a solid glass blank, a powder green compact or in the form of a powder, is then subjected to at least one heat treatment in the range of from 450 to 1050° C. It is preferred that a first heat treatment is initially carried out at a temperature in the range of from 480 to 580° C., in particular 480 to 560° C. and preferably 480 to 520° C. to produce a glass with nuclei which are suitable for forming lithium metasilicate and/or lithium disilicate crystals. This first heat treatment is preferably carried out for a period of from 5 to 120 minutes, in particular 10 to 60 minutes and preferably 10 to 30 minutes. The glass with nuclei can then preferably be subjected to at least one further temperature treatment at a higher temperature and in particular more than 580° C. to effect crystallization of lithium metasilicate or lithium disilicate. This further heat treatment is preferably carried out for a period of from 10 to 120 minutes, in particular 10 to 60 minutes and particularly preferably 20 to 30 minutes. To crystallize lithium metasilicate, the further heat treatment is usually carried out at 600 to 950° C., preferably 620 to 850° C. and quite particularly preferably 650 to 750° C. To crystallize lithium disilicate, the further heat treatment is usually carried out at 750 to 1050° C., preferably 800 to 1000° C., particularly preferably 820 to 950° C. and quite particularly preferably 850 to 900° C.

The lithium silicate glass ceramic used according to the invention and the lithium silicate glass used according to the invention are present in particular in the form of powders, granulates or blanks, e.g. monolithic blanks, such as discs, cuboids or cylinders, or powder green compacts, in unsintered, partly sintered or densely-sintered form. They can easily be further processed in these forms. However, they can also be present in the form of an overstructure for dental restorations, such as in particular crowns. It is preferred that the glass ceramic or the glass is shaped into the desired geometry by machining or pressing.

The lithium silicate glass ceramic used according to the invention and the lithium silicate glass used according to the invention are suitable in particular for coating oxide ceramics, metals and alloys.

In a preferred embodiment, the substrate is an oxide ceramic. Zirconium oxide ceramics are particularly preferred. Examples of suitable zirconium oxide ceramics are ceramics based on polycrystalline tetragonal zirconium oxide (tetragonal zirconia polycrystal, TZP) in which the tetragonal form is stabilized by the addition of $Y_2O_3$ and/or $CeO_2$.

In another preferred embodiment, the substrate is a metal or an alloy. Non-precious metal alloys and in particular non-ferrous alloys which are suitable for dental applications are particularly preferred. Examples of suitable alloys are in particular alloys of the Ni—Cr, Co—Cr and Co—Cr—W type.

It is furthermore preferred that the substrate is a dental restoration and in particular a bridge, an inlay, an onlay, a veneer, an abutment, a partial crown, a crown or a facet.

The invention also relates to a process for coating a substrate selected from oxide ceramics, metals and alloys, in which a lithium silicate glass ceramic as described above or a lithium silicate glass as described above are applied to the substrate. The substrate is preferably a preferred substrate as described above.

In an embodiment of the process according to the invention, the lithium silicate glass ceramic or the lithium silicate glass is applied to the substrate by sintering and preferably by pressing-on.

During sintering, the lithium silicate glass ceramic according to the invention or the lithium silicate glass according to the invention is applied in customary manner, e.g. as powder, to the material to be coated and then sintered at increased temperature.

During the preferred pressing-on, the lithium silicate glass ceramic according to the invention or the lithium silicate glass according to the invention, e.g. in the form of powder green compacts or monolithic blanks, is converted to a viscous state at an increased temperature of e.g. 700 to 1200° C. and pressed onto the substrate using low pressure, e.g. 2 to 10 bar. For this, in particular the methods described in EP 231 773 A1 and the press furnace disclosed there can be used. A suitable furnace is e.g. the Programat EP 5000 from Ivoclar Vivadent AG.

In another embodiment of the process according to the invention, the lithium silicate glass ceramic or the lithium silicate glass is applied to the substrate by joining. Suitable joining methods are known per se and comprise for example joining by means of a glass or glass ceramic solder, joining by adhesion by means of an adhesive or dental cement, joining by sagging by means of a temperature treatment in which the materials to be joined are softened, and joining by friction welding or wringing.

In a particularly preferred embodiment, the lithium silicate glass ceramic or the lithium silicate glass is shaped to a desired geometry by hot pressing or by machining before joining.

The hot pressing is usually carried out at increased pressure and increased temperature. It is preferred that the hot pressing is carried out at a temperature of from 700 to 1200° C. It is further preferred to carry out the hot pressing at a pressure of from 2 to 10 bar. The desired shape change is achieved by viscous flow of the material used. The lithium metasilicate glass ceramic according to the invention, the lithium disilicate glass ceramic according to the invention, the lithium silicate glass according to the invention and in particular the lithium silicate glass with nuclei according to the invention can be used for the hot pressing. The glass ceramics and glasses can be used in particular in the form of blanks, e.g. solid blanks or powder green compacts, e.g. in unsintered, partly sintered or densely-sintered form.

The machining is usually carried out by material removal processes and in particular by milling and/or grinding. It is particularly preferred that the machining is carried out as part of a CAD/CAM process. For the machining, the lithium silicate glass, the lithium silicate glass with nuclei, the lithium metasilicate and lithium disilicate glass ceramic can be used. The glasses and glass ceramics can be used in particular in the form of blanks, e.g. solid blanks or powder green compacts, e.g. in unsintered, partly sintered or densely-sintered form. For the machining, lithium silicate glass ceramic in particular with lithium disilicate and preferably with lithium metasilicate as main crystal phase is preferably used. The lithium silicate glass ceramic can also be used in a not yet fully crystallized form which was produced by heat treatment at a lower temperature. This has the advantage that an easier machining and thus the use of simpler equipment for the machining is possible. After the machining of such a partly crystallized material, the latter is usually subjected to a heat treatment at a higher temperature and in particular 750 to 1050° C., preferably 800 to 950° C. and particularly preferably about 850 to 900° C. in order to effect further crystallization of lithium metasilicate or preferably lithium disilicate.

In general, the lithium silicate glass ceramic or the lithium silicate glass can also in particular be heat-treated after the shaping by hot pressing or machining, in order to convert precursors used, such as lithium silicate glass, lithium silicate glass with nuclei or lithium metasilicate glass ceramic, to lithium meta- and/or disilicate glass ceramic, increase the crystallization of lithium meta- and/or disilicate, or reduce the porosity e.g. of a porous powder green compact used.

It is preferred that, after the coating procedure has been completed, a coating is obtained which comprises a lithium silicate glass ceramic with lithium meta- and/or disilicate as main crystal phase as it has particularly good properties. Glass ceramics which have the crystal phases and mechanical properties described above are particularly preferred.

Furthermore, the invention relates to a composite material which comprises a lithium silicate glass ceramic as defined above or a lithium silicate glass as defined above on a substrate selected from oxide ceramics, metals and alloys. All embodiments are preferred which are also given as preferred for the lithium silicate glass ceramic used according to the invention, the lithium silicate glass used according to the invention as well as the substrate. The composite material can be produced in particular by means of the process according to the invention.

The invention also relates to a lithium silicate glass ceramic which comprises the following components

| Component | wt.-% |
|---|---|
| $SiO_2$ | 56.0 to 72.5, in particular 56.9 to 72.0 |
| $Li_2O$ | 13.0 to 19.0, in particular 14.2 to 18.0 |
| $Rb_2O$ | 3.0 to 9.0, in particular 3.7 to 7.7 |
| $Al_2O_3$ | 2.0 to 5.0, in particular 2.5 to 4.5 |
| $P_2O_5$ | 2.0 to 6.0, in particular 3.1 to 5.0 |
| $ZrO_2$ | 0 to 4.5, in particular 0 to 4.0 |
| Transition metal oxide | 0 to 7.5, in particular 0 to 7.0, | wherein the transition metal oxide is selected from the group consisting of oxides of yttrium, oxides of transition metals with an atomic number from 41 to 79 and mixtures of these oxides.

Moreover, the invention also relates to a lithium silicate glass which comprises the components of the above glass ceramic.

In addition, the lithium silicate glass and the lithium silicate glass ceramic can also comprise still further components such as are given above for the lithium silicate glass ceramic used according to the invention and the lithium silicate glass used according to the invention. All embodiments are preferred which are also given as preferred for the lithium silicate glass ceramic used according to the invention and the lithium silicate glass used according to the invention.

The invention is explained in more detail below by means of examples.

EXAMPLES

A total of 15 glasses and glass ceramics according to the invention with the compositions given in Table I were produced by melting corresponding starting glasses followed by heat treatment for controlled nucleation and crystallization.

For this, the starting glasses in an amount of 100 to 200 g were first melted from customary raw materials at 1450 to 1550° C., wherein the melting was very easily possible without formation of bubbles or streaks. By pouring the starting glasses into water, glass frits were produced which were then melted a second time at 1450 to 1550° C. for 1 to 3 h for homogenization. The obtained glass melts were then poured into pre-heated moulds to produce glass monoliths. All glass monoliths proved transparent.

The glass monoliths were then converted to glasses and glass ceramics according to the invention by thermal treatment. The thermal treatments used for controlled nucleation and controlled crystallization are also given in Table I. The following meanings apply

| | |
|---|---|
| $T_N$ and $t_N$ | Temperature and time used for nucleation |
| $T_C$ and $t_C$ | Temperature and time used for first crystallization |
| $T_{FC}$ and $t_{FC}$ | Temperature and time used for final crystallization |
| $T_{press}$ and $t_{press}$ | Temperature and time used for hot pressing |

It can be seen that a first heat treatment in the range of from 470 to 500° C. resulted in the formation of lithium silicate glasses with nuclei and these glasses crystallized as a result of further heat treatment at 600 to 710° C. (Examples 1-6, 8-9 and 13) to form glass ceramics with lithium metasilicate as main crystal phase or as a result of heat treatment at 880° C. (Examples 7 and 14) directly to form glass ceramics with lithium disilicate as main crystal phase, as was established by X-ray diffraction tests. A final heat treatment at a temperature of from 860 to 950° C. (Examples 1, 3-4, 6-8, 10-12 and 14) finally resulted in the formation of glass ceramics with lithium disilicate as main crystal phase. By contrast, a final heat treatment at a temperature of only 820 to 840° C. (Examples 2, 5, 9 and 13) resulted in the formation of glass ceramics with lithium metasilicate as main crystal phase.

The produced lithium disilicate glass ceramics had high fracture toughness values, measured as critical stress intensity factor $K_{IC}$ according to the SEVNB method, of more than 2 MPa·m$^{0.5}$ and in particular even at least 2.3 MPa·m$^{0.5}$.

The biaxial strength GB was also high, at more than 400 MPa and up to more than 600 MPa. It was determined according to dental standard ISO 6872 (2008) on test pieces that were produced by machining of the respective lithium disilicate glass ceramic. A CEREC-InLab machine (Sirona, Bensheim) was used for the processing.

They were also able to be applied by hot pressing as coatings in particular onto oxide ceramic restorations or metal restorations, e.g. in order to veneer them as desired.

TABLE I

| | Example | | | | | | | | | |
|---|---|---|---|---|---|---|---|---|---|---|
| Composition | 1 wt.-% | 2 wt.-% | 3 wt.-% | 4 wt.-% | 5 wt.-% | 6 wt.-% | 7 wt.-% | 8 wt.-% | 9 wt.-% | 10 wt.-% |
| $SiO_2$ | 70.9 | 59.9 | 72.0 | 70.0 | 56.9 | 69.1 | 68.9 | 69.4 | 57.1 | 70.0 |
| $Li_2O$ | 14.8 | 18.0 | 15.0 | 14.5 | 15.5 | 14.4 | 14.9 | 14.5 | 16.0 | 14.5 |
| $Rb_2O$ | 7.7 | 7.7 | 6.3 | 6.1 | 7.7 | 6.0 | 3.7 | 6.1 | 7.7 | 6.1 |
| $Al_2O_3$ | 3.4 | 3.5 | 3.4 | 3.2 | 3.4 | 3.3 | 3.0 | 3.2 | 3.5 | 3.2 |
| $P_2O_5$ | 3.2 | 3.4 | 3.3 | 3.3 | 3.3 | 3.1 | 4.0 | 3.3 | 5.0 | 3.3 |
| $Na_2O$ | — | — | — | — | — | — | — | — | — | — |
| $K_2O$ | — | — | — | — | — | — | 1.4 | — | — | — |
| $Cs_2O$ | — | — | — | — | — | — | — | — | — | — |
| MgO | — | — | — | — | 0.3 | 0.3 | — | — | — | — |
| CaO | — | — | — | — | — | — | — | — | 3.0 | — |
| $Y_2O_3$ | — | — | — | — | — | — | — | — | — | — |
| $La_2O_3$ | — | — | — | — | — | — | — | — | 1.5 | — |
| $GeO_2$ | — | — | — | — | 8.0 | — | — | — | 0.8 | — |
| $ZrO_2$ | — | 5.0 | — | 0.4 | 2.0 | 0.9 | 1.4 | 0.8 | 2.0 | 0.4 |
| $CeO_2$ | — | 2.0 | — | 1.8 | 2.0 | 2.0 | 1.8 | 1.9 | 2.0 | 1.8 |
| $V_2O_5$ | — | 0.1 | — | 0.1 | 0.1 | 0.1 | 0.1 | 0.1 | 0.1 | 0.1 |
| $Tb_4O_7$ | — | 0.3 | — | 0.5 | 0.5 | 0.5 | 0.5 | 0.5 | 0.5 | 0.5 |
| $Er_2O_3$ | — | 0.1 | — | 0.1 | 0.3 | 0.3 | 0.3 | 0.2 | 0.3 | 0.1 |
| F | — | — | — | — | — | — | — | — | 0.5 | — |
| $T_g$/° C. | 471 | 476 | 468 | 468 | 465 | 471 | 467 | 477 | 447 | 468 |
| $T_N$/° C. | 490 | 500 | 490 | 490 | 480 | 490 | 500 | 500 | 470 | 490 |
| $t_N$/min | 10 | 30 | 10 | 10 | 10 | 10 | 10 | 10 | 10 | 10 |
| $T_C$/° C. | 700 | 700 | 700 | 700 | 620 | 710 | 880 | 700 | 660 | |
| $t_C$/min | 20 | 20 | 20 | 20 | 40 | 20 | 30 | 20 | 30 | |
| Main crystal phase | $Li_2SiO_3$ | $Li_2SiO_3$ | $Li_2SiO_3$ | $Li_2SiO_3$ | $Li_2SiO_3$ | $Li_2SiO_3$ | $Li_2Si_2O_5$ | $Li_2SiO_3$ | $Li_2SiO_3$ | |
| Other crystal phases | | | $Li_2Si_2O_5$ | $Li_2Si_2O_5$ | | $Li_2Si_2O_5$ | $Li_3PO_4$ | $Li_2Si_2O_5$ | | |
| $T_{FC}$/° C. | 880 | 820 | 880 | 870 | 830 | 860 | | 870 | 820 | |
| $t_{FC}$/min | 7 | 20 | 7 | 7 | 7 | 7 | | 7 | 10 | |
| $T_{press}$/° C. | | | | | | | 950 | | | 930 |
| $t_{press}$/min | | | | | | | 25 | | | 25 |

TABLE I-continued

| Main crystal phase | $Li_2Si_2O_5$ | $Li_2SiO_3$ | $Li_2Si_2O_5$ | $Li_2Si_2O_5$ | $Li_2SiO_3$ | $Li_2Si_2O_5$ | $Li_2Si_2O_5$ | $Li_2Si_2O_5$ | $Li_2SiO_3$ | $Li_2Si_2O_5$ |
|---|---|---|---|---|---|---|---|---|---|---|
| Other crystal phases | $Li_2SiO_3$ $Li_3PO_4$ | $Li_3PO_4$ | $Li_3PO_4$ | $Li_3PO_4$ | $Li_2Si_2O_5$ $Li_3PO_4$ | $Li_3PO_4$ | $Li_3PO_4$ | $Li_3PO_4$ | $Li_3PO_4$ $Ca_5(PO_4)_3F$ | $Li_3PO_4$ |
| L* | | | | 76.50 | | 71.90 | 79.11 | 73.26 | | |
| a* | | | | 3.37 | | 9.34 | 6.32 | 8.40 | | |
| b* | | | | 20.96 | | 25.32 | 31.80 | 26.42 | | |
| CR | | | | 89.85 | | 84.79 | 68.55 | 84.29 | | |
| $CTE_{100-400°C}/10^{-6} \cdot K^{-1}$ | | 12.8 | 9.70 | | 11.7 | | 9.70 | | 12.0 | |
| $K_{IC}/MPa\ m^{0.5}$ | | | | | | | | | | |
| $\sigma_B$/MPa | 687 | | 576 | | | | | | | |

| Composition | Example 11 wt.-% | Example 12 wt.-% | Example 13 wt.-% | Example 14 wt.-% | Example 15 wt.-% |
|---|---|---|---|---|---|
| $SiO_2$ | 69.1 | 69.4 | 63.3 | 68.6 | 69.5 |
| $Li_2O$ | 14.4 | 14.5 | 18.0 | 14.2 | 14.4 |
| $Rb_2O$ | 6.0 | 6.1 | 7.7 | 7.4 | 5.4 |
| $Al_2O_3$ | 3.3 | 3.2 | 3.5 | 2.5 | 4.5 |
| $P_2O_5$ | 3.1 | 3.3 | 3.4 | 3.4 | 3.4 |
| $Na_2O$ | — | — | — | — | — |
| $K_2O$ | — | — | — | — | — |
| $Cs_2O$ | — | — | — | — | 1.0 |
| MgO | 0.3 | — | — | — | — |
| CaO | — | — | — | — | — |
| $Y_2O_3$ | — | — | 3.0 | — | — |
| $La_2O_3$ | — | — | — | — | — |
| $GeO_2$ | — | — | — | — | — |
| $ZrO_2$ | 0.9 | 0.8 | — | 1.5 | 1.8 |
| $CeO_2$ | 2.0 | 1.9 | 1.0 | 1.7 | — |
| $V_2O_5$ | 0.1 | 0.1 | 0.1 | 0.1 | — |
| $Tb_4O_7$ | 0.5 | 0.5 | — | 0.5 | — |
| $Er_2O_3$ | 0.3 | 0.2 | — | 0.1 | — |
| F | — | — | — | — | — |
| $T_g/°C$ | 471 | 477 | 460 | 480 | |
| $T_N/°C$ | 490 | 500 | 480 | 500 | |
| $t_N$/min | 10 | 10 | 10 | 10 | |
| $T_C/°C$ | | | 600 | 880 | |
| $t_C$/min | | | 60 | 30 | |
| Main crystal phase | | | $Li_2SiO_3$ | $Li_2Si_2O_5$ | |
| Other crystal phases | | | | $Li_3PO_4$ | |
| $T_{FC}/°C$ | | | 840 | | |
| $t_{FC}$/min | | | 10 | | |
| $T_{press}/°C$ | 940 | 930 | | 950 | |
| $t_{Press}$/min | 25 | 25 | | 25 | |
| Main crystal phase | $Li_2Si_2O_5$ | $Li_2Si_2O_5$ | $Li_2SiO_3$ | $Li_2Si_2O_5$ | |
| Other crystal phases | $Li_3PO_4$ | $Li_3PO_4$ | $Li_3PO_4$ | $Li_3PO_4$ | |
| L* | 71.18 | | | 81.27 | |
| a* | 10.29 | | | 2.93 | |
| b* | 32.91 | | | 24.26 | |
| CR | 75.60 | | | 69.77 | |
| $CTE_{100-400°C}/10^{-6} \cdot K^{-1}$ | | | 12.4 | 9.6 | |
| $K_{IC}/MPa\ m^{0.5}$ | 2.30 | | | | |
| $\sigma_B$/MPa | 411 | | | | |

L*, a*, b*: colour coordinates of the samples, determined according to DIN 5033 and DIN 6174
CR: contrast value as a measure of the translucence, determined according to BS 5612

The invention claimed is:
1. Composite material which comprises a lithium silicate glass ceramic or a lithium silicate glass, which comprise the following components

| Component | wt.-% |
|---|---|
| $SiO_2$ | 56.0 to 73.0 |
| $Li_2O$ | 13.0 to 19.0 |
| $Rb_2O$ | 3.0 to 9.0 |
| $Al_2O_3$ | 2.0 to 5.0 |
| $P_2O_5$ | 2.0 to 6.0 |
| $ZrO_2$ | 0 to 4.5 | on a substrate selected from oxide ceramics, metals and alloys.

2. Composite material according to claim 1, wherein the substrate is a dental restoration.

3. Process for coating a substrate selected from oxide ceramics, metals and alloys, in which a lithium silicate glass ceramic or a lithium silicate glass which comprise the following components

| Component | wt.-% |
|---|---|
| $SiO_2$ | 56.0 to 73.0 |
| $Li_2O$ | 13.0 to 19.0 |
| $Rb_2O$ | 3.0 to 9.0 |
| $Al_2O_3$ | 2.0 to 5.0 |
| $P_2O_5$ | 2.0 to 6.0 |
| $ZrO_2$ | 0 to 4.5 | is applied to the substrate.

4. Process according to claim 3, in which the lithium silicate glass ceramic or the lithium silicate glass comprise at least one of the following components in the given amounts

| Component | wt.-% |
|---|---|
| $SiO_2$ | 56.9 to 72.0 |
| $Li_2O$ | 14.2 to 18.0 |
| $Rb_2O$ | 3.7 to 7.7 |
| $Al_2O_3$ | 2.5 to 4.5 |
| $P_2O_5$ | 3.1 to 5.0 |
| $ZrO_2$ | 0 to 4.0 |
| Transition metal oxide | 0 to 7.5, | wherein the transition metal oxide is selected from the group consisting of oxides of yttrium, oxides of transition metals with an atomic number from 41 to 79 and mixtures of these oxides.

5. Process according to claim 3, in which the lithium silicate glass ceramic or the lithium silicate glass comprise 58.0 to 72.0 wt.-% $SiO_2$.

6. Process according to claim 3, in which the lithium silicate glass ceramic or the lithium silicate glass comprise 3.7 to 7.7 wt.-% $Rb_2O$.

7. Process according to claim 3, in which the lithium silicate glass ceramic or the lithium silicate glass comprise 2.5 to 4.0 wt.-% $Al_2O_3$.

8. Process according to claim 3, in which the lithium silicate glass ceramic or the lithium silicate glass comprise less than 2.5 wt.-% $Cs_2O$.

9. Process according to claim 3, in which the lithium silicate glass ceramic or the lithium silicate glass comprise less than 4.0 wt.-% $Na_2O$ and/or $K_2O$.

10. Process according to claim 3, in which the lithium silicate glass ceramic or the lithium silicate glass comprise less than 3.8 wt.-% $BaO$.

11. Process according to claim 3, in which a lithium silicate glass ceramic is used which comprises lithium metasilicate as main crystal phase and has a bending strength in the range of about 180 to 300 MPa and/or a fracture toughness, measured as $K_{IC}$ value, of at least about 2.0 $MPa \cdot m^{0.5}$.

12. Process according to claim 11, wherein the fracture toughness, measured as $K_{IC}$ value, is at least about 2.3 $MPa \cdot m^{0.5}$.

13. Process according to claim 3, in which a lithium silicate glass ceramic is used which comprises lithium disilicate as main crystal phase and has a bending strength in the range of about 400 to 700 MPa and/or a fracture toughness, measured as $K_{IC}$ value, of at least about 2.0 $MPa \cdot m^{0.5}$.

14. Process according to claim 13, wherein the fracture toughness, measured as $K_{IC}$ value, is at least about 2.3 $MPa \cdot m^{0.5}$.

15. Process according to claim 3, in which a lithium silicate glass is used.

16. Process according to claim 15, wherein the lithium silicate glass comprises nuclei which are suitable for forming lithium metasilicate and/or lithium disilicate crystals.

17. Process according to claim 3, in which the substrate is an oxide ceramic.

18. Process according to claim 17, in which the substrate comprises a zirconium oxide ceramic.

19. Process according to claim 3, in which the substrate is a metal or an alloy.

20. Process according to claim 19, wherein the alloy comprises a non-precious metal alloy.

21. Process according to claim 3, in which the substrate is a dental restoration.

22. Process according to claim 21, wherein the dental restoration comprises a bridge, an inlay, an onlay, a veneer, an abutment, a partial crown, a crown or a facet.

23. Process according to claim 3, in which the lithium silicate glass ceramic or the lithium silicate glass is applied to the substrate by sintering.

24. Process according to claim 3, in which the lithium silicate glass ceramic or the lithium silicate glass is applied to the substrate by joining.

25. Process according to claim 24, in which the lithium silicate glass ceramic or the lithium silicate glass is shaped to a desired geometry by machining or by hot pressing before joining.

26. Process according to claim 3, in which a coating is obtained which comprises a lithium silicate glass ceramic that comprises lithium disilicate as main crystal phase, and which has a bending strength in the range of about 400 to 700 MPa and/or a fracture toughness, measured as $K_{IC}$ value, of at least about 2.0 $MPa \cdot m^{0.5}$.

27. Process according to claim 26, wherein the fracture toughness, measured as $K_{IC}$ value, is at least about 2.3 $MPa \cdot m^{0.5}$.

28. Process according to claim 3, in which the lithium silicate glass ceramic or the lithium silicate glass comprise at least one of the following components in the given amounts

| Component | wt.-% |
|---|---|
| $SiO_2$ | 56.9 to 72.0 |
| $Li_2O$ | 14.2 to 18.0 |

-continued

| Component | wt.-% |
|---|---|
| $Rb_2O$ | 3.7 to 7.7 |
| $Al_2O_3$ | 2.5 to 4.5 |
| $P_2O_5$ | 3.1 to 5.0 |
| $ZrO_2$ | 0 to 4.0 |
| Transition metal oxide | 0 to 7.0. |

29. Process according to claim 3, in which the lithium silicate glass ceramic or the lithium silicate glass comprise 60.0 to 71.0 wt.-% $SiO_2$.

30. Process according to claim 3, in which the lithium silicate glass ceramic or the lithium silicate glass comprise 3.0 to 3.5 wt.-% $Al_2O_3$.

31. Process according to claim 3, in which the lithium silicate glass ceramic or the lithium silicate glass comprise less than 1.5 wt.-% $Cs_2O$.

32. Process according to claim 3, in which the lithium silicate glass ceramic or the lithium silicate glass is substantially free of $Cs_2O$.

33. Process according to claim 3, in which the lithium silicate glass ceramic or the lithium silicate glass comprise less than 3.5 wt.-% $Na_2O$ and/or $K_2O$.

34. Process according to claim 3, in which the lithium silicate glass ceramic or the lithium silicate glass comprise less than 2.0 wt.-% $Na_2O$ and/or $K_2O$.

35. Process according to claim 3, in which the lithium silicate glass ceramic or the lithium silicate glass comprise less than 2.5 wt.-% BaO.

36. Process according to claim 3, in which the lithium silicate glass ceramic or the lithium silicate glass is substantially free of BaO.

37. Process according to claim 3, in which the lithium silicate glass ceramic or the lithium silicate glass is applied to the substrate by pressing-on.

38. Process according to claim 3, in which a lithium silicate glass ceramic is used which comprises lithium metasilicate as main crystal phase.

39. Process according to claim 3, in which a lithium silicate glass ceramic is used which comprises lithium disilicate as main crystal phase.

40. Process according to claim 3, in which a coating is obtained which comprises a lithium silicate glass ceramic that comprises lithium metasilicate as main crystal phase.

41. Process according to claim 3, in which a coating is obtained which comprises a lithium silicate glass ceramic that comprises lithium disilicate as main crystal phase.

42. Process for coating a substrate selected from oxide ceramics, metals and alloys, in which a lithium silicate glass ceramic or a lithium silicate glass which comprise the following components

| Component | wt.-% |
|---|---|
| $SiO_2$ | 56.0 to 73.0 |
| $Li_2O$ | 13.0 to 19.0 |
| $Rb_2O$ | 3.0 to 9.0 |
| $Al_2O_3$ | 2.0 to 5.0 |
| $P_2O_5$ | 2.0 to 6.0 | is applied to the substrate and in which a coating is obtained which comprises a lithium silicate glass ceramic that comprises lithium metasilicate as main crystal phase, and which has a bending strength in the range of about 180 to 300 MPa and/or a fracture toughness, measured as $K_{IC}$ value, of at least about 2.0 MPa·m$^{0.5}$.

43. Process according to claim 42, wherein the fracture toughness, measured as $K_{IC}$ value, is at least about 2.3 MPa·m$^{0.5}$.

44. Lithium silicate glass ceramic, which comprises the following components in the given amounts

| Component | wt.-% |
|---|---|
| $SiO_2$ | 56.0 to 72.5 |
| $Li_2O$ | 13.0 to 19.0 |
| $Rb_2O$ | 3.0 to 9.0 |
| $Al_2O_3$ | 2.0 to 5.0 |
| $P_2O_5$ | 2.0 to 6.0 |
| $ZrO_2$ | 0 to 4.5 |
| Transition metal oxide | 0 to 7.5, | wherein the transition metal oxide is selected from the group consisting of oxides of yttrium, oxides of transition metals with an atomic number from 41 to 79 and mixtures of these oxides.

45. Lithium silicate glass, which comprises the components of the glass ceramic according to claim 44.

46. Lithium silicate glass ceramic, which comprises the following components in the given amounts

| Component | wt.-% |
|---|---|
| $SiO_2$ | 56.9 to 72.0 |
| $Li_2O$ | 14.2 to 18.0 |
| $Rb_2O$ | 3.7 to 7.7 |
| $Al_2O_3$ | 2.5 to 4.5 |
| $P_2O_5$ | 3.1 to 5.0 |
| $ZrO_2$ | 0 to 4.0 |
| Transition metal oxide | 0 to 7.0, | wherein the transition metal oxide is selected from the group consisting of oxides of yttrium, oxides of transition metals with an atomic number from 41 to 79 and mixtures of these oxides.

* * * * *